US012569118B2

(12) United States Patent
Ozaki et al.

(10) Patent No.: US 12,569,118 B2
(45) Date of Patent: Mar. 10, 2026

(54) ENDOSCOPE SYSTEM AND PACKAGING MATERIALS FOR ENDOSCOPE

(71) Applicant: OLYMPUS MEDICAL SYSTEMS CORP., Tokyo (JP)

(72) Inventors: Akira Ozaki, Hachioji (JP); Masahiro Ashizuka, Hino (JP); Takeo Suzuki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 366 days.

(21) Appl. No.: 18/116,899

(22) Filed: Mar. 3, 2023

(65) Prior Publication Data

US 2023/0277040 A1      Sep. 7, 2023

Related U.S. Application Data

(60) Provisional application No. 63/317,188, filed on Mar. 7, 2022.

(51) Int. Cl.
*A61B 1/00*          (2006.01)
(52) U.S. Cl.
CPC ...... *A61B 1/00096* (2013.01); *A61B 1/00124* (2013.01); *A61B 1/00009* (2013.01)
(58) Field of Classification Search
CPC ............ A61B 1/00103; A61B 1/00114; A61B 1/00144; A61B 1/00131
See application file for complete search history.

(56) References Cited

U.S. PATENT DOCUMENTS 4,779,611 A * 10/1988 Grooters ............ A61B 1/00082
                                                        600/116
5,168,863 A * 12/1992 Kurtzer .............. A61B 1/00142
                                                        600/122
(Continued)

FOREIGN PATENT DOCUMENTS

CN          1878496 A     12/2006
CN         101461703 A     6/2009
(Continued)

OTHER PUBLICATIONS

Office Action dated Nov. 26, 2025, issued in corresponding Chinese Patent Application No. 202310205461.1.

*Primary Examiner* — Anh Tuan T Nguyen
*Assistant Examiner* — Shankar Raj Ghimire
(74) *Attorney, Agent, or Firm* — Morgan, Lewis & Bockius LLP

(57)          ABSTRACT
An endoscope system, comprising: an endoscope including an insertion portion, an operation portion, and a connector configured to be connected to an external apparatus, wherein the insertion portion includes a bending portion and wherein the operation portion is connected to the insertion portion; a packaging material, wherein the packaging material contains at least the insertion portion or the operation portion in a sterile environment; and a dome-shaped portion formed in the packaging material, wherein the dome-shaped portion defines a space, and at least a distal section of the bending portion is located inside the space, where in a maximum bent position, the distal section of the bending portion does not contact an inner surface of the dome shaped portion, and wherein the connector is disposed outside of the packaging material.

14 Claims, 8 Drawing Sheets

(56) References Cited

U.S. PATENT DOCUMENTS

| | | | | |
|---|---|---|---|---|
| 5,237,984 A * | 8/1993 | Williams, III | ..... | A61B 1/00142 |
| | | | | 604/263 |
| 5,274,500 A * | 12/1993 | Dunn | ...................... | A61B 1/042 |
| | | | | 359/507 |
| 5,575,752 A * | 11/1996 | Yabe | ................... | A61B 1/00144 |
| | | | | 600/122 |
| 5,630,787 A * | 5/1997 | Yabe | ...................... | A61B 1/012 |
| | | | | 600/122 |
| 5,690,605 A * | 11/1997 | Hamlin | ................ | A61B 5/0088 |
| | | | | 600/125 |
| 5,695,449 A * | 12/1997 | Moriyama | ......... | A61B 1/00142 |
| | | | | 600/122 |
| 5,813,409 A * | 9/1998 | Leahy | .................... | A61B 46/00 |
| | | | | 128/850 |
| 5,873,814 A * | 2/1999 | Adair | ................. | A61B 1/00052 |
| | | | | 600/109 |
| 5,924,977 A * | 7/1999 | Yabe | ................... | A61B 1/00142 |
| | | | | 600/122 |
| 7,764,304 B2 * | 7/2010 | Meron | ............... | A61B 1/00144 |
| | | | | 600/114 |
| 8,317,689 B1 * | 11/2012 | Remijan | ................ | A61B 1/042 |
| | | | | 600/125 |
| 11,071,534 B2 * | 7/2021 | Piskun | ............... | A61B 17/0218 |
| 11,246,674 B1 * | 2/2022 | Galbierz | ................ | A61G 10/02 |
| 11,547,282 B2 * | 1/2023 | Weise | ................ | A61B 1/00114 |
| 2003/0107726 A1 * | 6/2003 | Hirt | ...................... | A61B 1/0655 |
| | | | | 356/73.1 |
| 2003/0192799 A1 * | 10/2003 | Addy | ..................... | B65D 75/32 |
| | | | | 206/439 |
| 2006/0193761 A1 | 8/2006 | Moriyama et al. | | |
| 2008/0255440 A1 | 10/2008 | Eilersen et al. | | |
| 2009/0158539 A1 | 6/2009 | Onishi et al. | | |
| 2009/0221872 A1 * | 9/2009 | Liddle | ................ | A61B 1/00144 |
| | | | | 600/121 |
| 2010/0234733 A1 * | 9/2010 | Wahlheim | ............ | A61B 8/4281 |
| | | | | 600/459 |
| 2012/0232342 A1 * | 9/2012 | Reydel | ..................... | A61B 1/31 |
| | | | | 600/116 |
| 2014/0180007 A1 * | 6/2014 | Edidin | ..................... | A61B 1/05 |
| | | | | 600/122 |
| 2015/0133960 A1 * | 5/2015 | Lohmeier | .............. | A61B 34/30 |
| | | | | 606/130 |
| 2015/0202009 A1 * | 7/2015 | Nussbaumer | .......... | A61B 46/10 |
| | | | | 128/856 |
| 2015/0366618 A1 * | 12/2015 | Higuchi | ................. | A61B 90/50 |
| | | | | 359/510 |
| 2016/0073862 A1 | 3/2016 | Matsuno et al. | | |
| 2016/0174818 A1 * | 6/2016 | Viering | .............. | A61B 1/00057 |
| | | | | 600/109 |
| 2017/0209027 A1 * | 7/2017 | Raj | .................... | A61B 1/00034 |
| 2018/0185018 A1 * | 7/2018 | Piskun | ................. | A61B 1/3132 |
| 2018/0263481 A1 | 9/2018 | Muratori et al. | | |
| 2018/0280101 A1 * | 10/2018 | Ueda | ...................... | A61B 46/10 |
| 2018/0296069 A1 * | 10/2018 | Matthison-Hansen | ...................... | |
| | | | | A61B 1/0057 |
| 2023/0128303 A1 * | 4/2023 | Ouyang | ................. | A61B 1/015 |
| | | | | 600/476 |
| 2023/0389777 A1 * | 12/2023 | Ubelhart | ............ | A61B 1/00096 |
| 2024/0065532 A1 * | 2/2024 | Wu | .......................... | A61B 1/04 |
| 2024/0090922 A1 * | 3/2024 | Kotseroglou | ...... | A61B 17/3478 |
| 2025/0082183 A1 * | 3/2025 | Ubelhart | ............ | A61B 1/00057 |

FOREIGN PATENT DOCUMENTS

| | | |
|---|---|---|
| CN | 105120790 A | 12/2015 |
| CN | 107106000 A | 8/2017 |
| CN | 110087526 A | 8/2019 |
| JP | H06-178755 A | 6/1994 |
| JP | H06-68712 U | 9/1994 |
| JP | H08-173376 A | 7/1996 |
| JP | 2003-072861 A | 3/2003 |
| JP | 2008-508971 A | 3/2008 |

* cited by examiner

ENDOSCOPE SYSTEM AND PACKAGING MATERIALS FOR ENDOSCOPE

CROSS-REFERENCE TO RELATED APPLICATION

This application is based on and claims priority under 35 U.S.C. § 119 to U.S. Provisional Application No. 63/317, 188, filed on Mar. 7, 2022, the entire contents of which are incorporated herein by reference.

BACKGROUND

1. Technical Field

The present disclosure relates to an endoscope system that packages at least a portion of an endoscope with a packaging material and a packaging material for endoscope.

2. Description of the Related Art

Conventionally, endoscopes have been used for observation of insides of subjects, and each have an insertion portion for insertion into the subject. When the endoscope is an electronic endoscope, the insertion portion has a distal end provided with an image pickup apparatus including an objective optical system and an image pickup device. Endoscopes include endoscopes of front-view types and endoscopes of side-view types according to arrangements of the image pickup apparatuses at the distal end portions of the insertion portions. Each endoscope of the front-view type is configured to observe in a longitudinal axis direction of the insertion portion. Each endoscope of the side-view type is configured to observe in a direction crossing the longitudinal axis of the insertion portion.

For example, a prior art describes an endoscope of a side-view type in which an observation window is arranged on a side surface of a distal end portion.

Endoscopes include reuse endoscopes that are used a plurality of times through reprocessing and single-use endoscopes that are used only once.

Each single-use endoscope is sterilized in a state of being sealed in a packaging material configured as a sterile package and shipped in a state in which sterilization is maintained. The single-use endoscopes are discarded after a single use and do not require reprocessing.

SUMMARY

An endoscope system, comprising: an endoscope including an insertion portion, an operation portion, and a connector configured to be connected to an external apparatus, wherein the insertion portion includes a bending portion and wherein the operation portion is connected to the insertion portion; a packaging material, wherein the packaging material contains at least the insertion portion or the operation portion in a sterile environment; and a dome-shaped portion formed in the packaging material, wherein the dome-shaped portion defines a space, wherein at least a distal section of the bending portion is located inside the space, wherein, in a maximum bent position, the distal section of the bending portion does not contact an inner surface of the dome shaped portion, and wherein the connector is disposed outside of the packaging material.

A packaging material for an endoscope, the packaging material comprising:

a packaging material body forming a sterile environment, wherein the packaging material is configured to contain a first portion of the endoscope in the sterile environment; a dome-shaped portion formed in the packaging material body, wherein an interior of the dome-shaped portion defines an interior space; and a seal formed at a predetermined position of the packaging material body, wherein the seal is configured to allow a second portion of the endoscope to be located outside the sterile environment.

DETAILED DESCRIPTION

Figure 1:
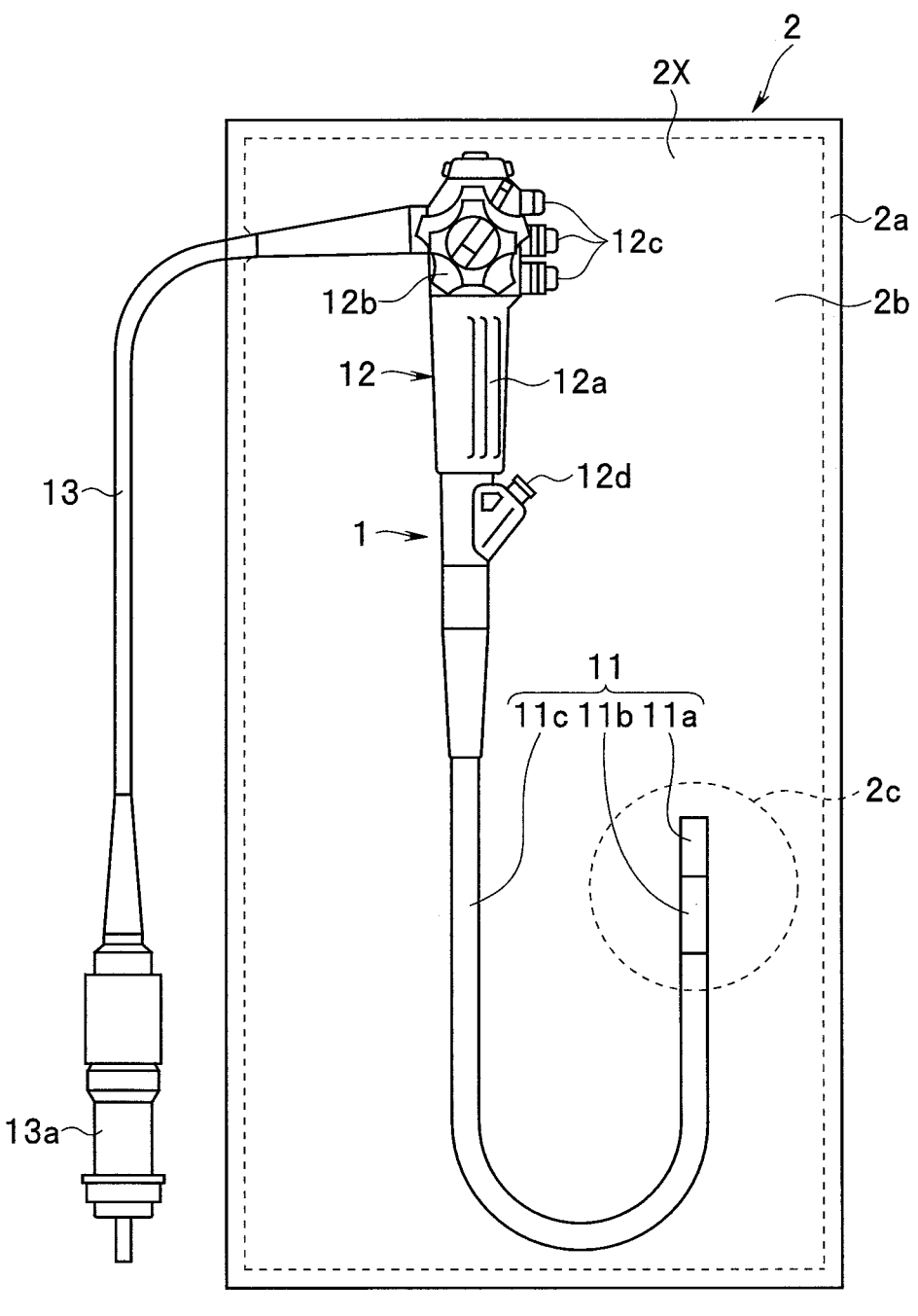
FIG. 1 is a plan view showing a configuration of an endoscope system according to a first embodiment.

In general, pre-use inspection of an endoscope is performed with the endoscope connected to an endoscope processor and a light source device, so a packaging material is unsealed to perform pre-use inspection. When a packaging material is unsealed, the endoscope is exposed to air in an endoscopy room. Then, there is risk in which environmental bacteria such as airborne bacteria and falling bacteria in the air adhere to the endoscope before the endoscope is inserted into a subject.

Therefore, it may be preferable that a time period from unsealing the packaging material to inserting the endoscope into the subject should be shortened as much as possible to shorten a time period through which the endoscope is exposed to air to maintain a sterile condition as much as possible.

According to embodiments to be described below, it is possible to provide an endoscope system and a packaging material for endoscope that can reduce risk of environmental bacteria adhering to the endoscope after the endoscope is removed from the packaging material.

The embodiments of the present disclosure will be described below with reference to the drawings, however, the present disclosure is not limited by the embodiments to be described below.

Note that the same or corresponding components in description of the drawings are denoted by the same reference numerals and characters as appropriate. Also note that the drawings are schematic, and length relationships of individual components, length ratios of the individual components, quantities of the individual components, or the like in one drawing may differ from reality for the sake of simplicity of explanation. Furthermore, portions may be included that are different from each other in length relationships and ratios among a plurality of the drawings.

First Embodiment

FIGS. 1 to 4 show a first embodiment of the present disclosure, and FIG. 1 is a plan view showing a configuration of an endoscope system in the first embodiment.

As shown in FIG. 1, the endoscope system includes an endoscope 1 and a packaging material 2. The endoscope 1 may be a single-use endoscope that is discarded (disposed of) after just a single use.

The endoscope 1 includes an insertion portion 11, an operation portion 12, and a universal cord 13.

The insertion portion 11 is a part that is inserted into a body cavity of a subject. Note that the subject into which the insertion portion 11 is inserted is assumed to be, for example, a living body of a human being or an animal.

The insertion portion 11 includes a distal end portion 11*a*, a bending portion 11*b*, and a flexible tube portion 11*c* in order from a distal end side to a proximal end side.

The endoscope 1 is configured, for example, as an electronic endoscope, and has the distal end portion 11*a* internally including an image pickup apparatus 14 (see FIGS. 2 and 3) configured to pick up an image of the subject. The image pickup apparatus 14 includes an objective optical system and an image pickup device (an image sensor), forms an optical image with the objective optical system, performs photoelectric conversion of the formed optical image with the image pickup device, and outputs image pickup signals.

Inside the insertion portion 11, a signal line, a light guide, a bending wire, a treatment instrument channel, or the like are disposed. The signal line is connected to the image pickup apparatus 14. The light guide transmits illumination light. The bending wire bends the bending portion 11*b*. Through the treatment instrument channel, a treatment instrument for endoscope is inserted.

The distal end portion 11*a* has a distal end surface on which an illumination window on the distal end side of the light guide, an observation window on the distal end side of the objective optical system, and an opening on the distal end side of the treatment instrument channel are arranged.

The bending portion 11*b* is a bendable part disposed on the proximal end side of the distal end portion 11*a*. The bending portion 11*b* is, for example, configured to be bendable in two directions, or four directions of up, down, left, and right.

Figure 2:
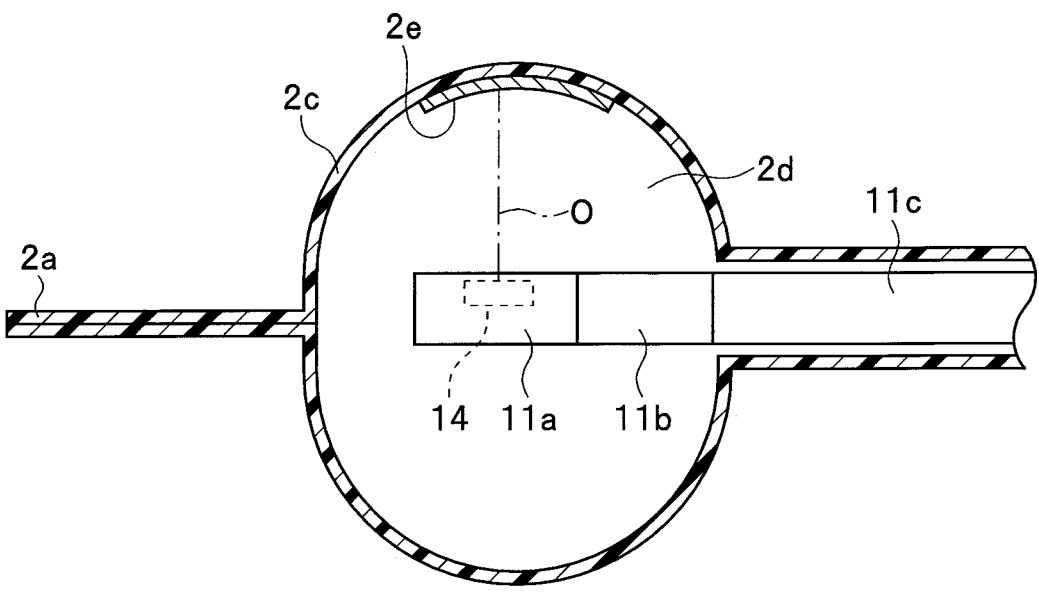
FIG. 2 is a cross-sectional view showing a configuration example of a dome-shaped portion of a packaging material provided corresponding to a side-viewing endoscope in the first embodiment.
Figure 3:
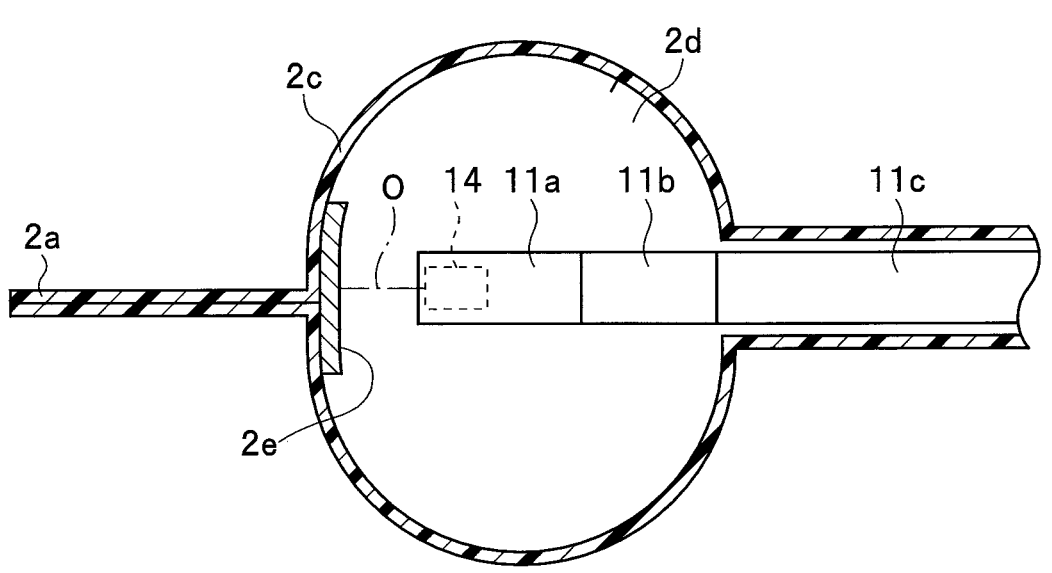
FIG. 3 is a cross-sectional view showing a configuration example of a dome-shaped portion of a packaging material provided corresponding to a front-viewing endoscope in the first embodiment.

When the bending portion 11*b* is bent, the direction of the distal end portion 11*a* changes, changing an observation direction of the image pickup apparatus 14 (a direction of an optical axis O of the objective optical system of the image pickup apparatus 14 shown in FIGS. 2 and 3) and the irradiation direction of the illumination light from the light guide. The bending portion 11*b* is also bent for better insertion performance of the insertion portion 11 inside the subject.

The flexible tube portion 11*c* is a tube portion that is disposed on the proximal end side of the bending portion 11*b* and has flexibility. Note that although the example here is a flexible endoscope including a flexible tube portion 11*c*, the endoscope may be a rigid endoscope having a configuration such that a portion corresponding to the flexible tube portion 11*c* is rigid.

The operation portion 12 is a part connected to the proximal end side of the insertion portion 11 for operation of the endoscope 1. The operation portion 12 includes a grasping portion 12*a*, a bending operation knob 12*b*, a plurality of operation buttons 12*c*, and a treatment instrument insertion opening 12*d*.

The grasping portion 12*a* is a part where an operator grasps the endoscope 1 with the palm.

The bending operation knob 12*b* is an operation device for operation to bend the bending portion 11*b* with, for example, the thumb of the hand grasping the grasping portion 12*a*. When the bending operation knob 12*b* is operated, the bending wire is pulled and the bending portion 11*b* is bent.

The plurality of operation buttons 12*c* include, for example, an air feeding and liquid feeding button, a suction button, and buttons related to image pickup. The air feeding and liquid feeding button is a button for operation of air feeding and liquid feeding to the observation window of the distal end portion 11*a* through an air feeding and liquid feeding channel (not shown) to clean the observation window. The suction button is a button for operation of aspirating a liquid, a mucous membrane, or the like from the inside of the subject, for example, through the treatment instrument channel that also serves as a suction channel. The buttons related to image pickup includes a button switch for release operation.

The treatment instrument insertion opening 12*d* is an opening on the proximal end side of the treatment instrument channel. Through the treatment instrument insertion opening 12*d*, various treatment instruments such as forceps are inserted into the treatment instrument channel. The distal end portion of the treatment instrument protrudes from the distal end side opening of the treatment instrument channel provided in the distal end portion 11*a* to perform various treatments.

One end of the universal cord 13 is connected to, for example, a lateral surface of the operation portion 12 on the proximal end side. The other end of the universal cord 13 is provided with a connector 13*a* to be connected to an external apparatus. Note that if the operation portion 12 is defined as a starting point, the one end of the universal cord 13 is a proximal end and the other end is a distal end. In the following, the proximal end, the distal end, or the like of the universal cord 13 is used for description instead of the one end and the other end.

Also, an example in which the connector 13*a* is provided at the distal end of the universal cord 13 is shown here. The configuration may also be such that the connector 13*a* is directly provided to the operation portion 12 or other part of the endoscope 1 without passing through the universal cord 13.

The packaging material 2 is configured as a sterile packaging material (sterile package). The packaging material 2 packs the insertion portion 11 and the operation portion 12, which are a first portion of the endoscope 1, in a packaging material body 2X to maintain the sterile condition of the insertion portion 11 and the operation portion 12. The connector 13*a*, which is a portion (a second portion) different from the first portion of the endoscope 1, is arranged outside the outer edge portion of the packaging material body 2X. The packaging material 2 (packaging material body 2X) is provided with a seal 2*a* at a predetermined position to seal a space 2b containing the insertion portion 11 and the operation portion 12. In the first embodiment, the seal 2a is provided on the outer edge portion of the packaging material 2 (the outer edge portion of the packaging material body 2X). The seal 2a is, for example, a heat seal formed in such a way that two sheets forming the packaging material 2 are heated and pressed to be fusion-bonded. Note that the portion where the universal cord 13 and the seal 2a overlap may be coated with an adhesive or a filler in addition to a heat seal. Such an adhesive or a filler can improve sealing performance.

In the space 2b sealed by the seal 2a, for example, the proximal end side of the universal cord 13 connected to the operation portion 12 is also arranged. A portion of the universal cord 13 and the connector 13a, which are portions other than the proximal end side of the universal cord 13, are arranged outside the packaging material 2. In other words, the universal cord 13 extends from the inside of the packaging material 2 to the outside through the seal 2a. Here, the portion of the universal cord 13 is a portion excluding the proximal end side of the universal cord 13 and the connector 13a.

FIG. 2 is a cross-sectional view showing a configuration example of a dome-shaped portion 2c of the packaging material 2 provided corresponding to a side-viewing endoscope in the first embodiment.

In the packaging material 2, the dome-shaped portion 2c having a bulge that differs from a bulge of the packaging material body 2X is formed integrally with the packaging material body 2X. The dome-shaped portion 2c internally includes a space 2d inside which the distal end portion 11a and the bending portion 11b are arranged. The space 2d within the dome-shaped portion 2c is formed in a size and shape that allows the bending portion 11b to bend freely.

The dome-shaped portion 2c includes a transparent or translucent portion on at least one side of the packaging material 2 so that the bending portion 11b is visible from the outside. The shape of the dome-shaped portion 2c may be any shape, including a sphere and a cube, as long as the bending portion 11b can freely bend.

Furthermore, the dome-shaped portion 2c includes, at least in part, a white area 2e for white balance. The white area 2e is disposed within the visual field in the direction of the optical axis O of the image pickup apparatus 14 when the bending portion 11b is in a neutral state in bending (a straight state in bending) in which the bending portion 11b is not bent. The endoscope 1 is packaged in the packaging material 2 with the bending portion 11b in the neutral state in bending. Therefore, the endoscope system is shipped with the white area 2e within the visual field of the image pickup apparatus 14.

FIG. 2 shows an example in which the endoscope 1 is a side-viewing endoscope, and the direction of the optical axis O of the objective optical system of the image pickup apparatus 14 is a direction crossing the longitudinal axis direction of the insertion portion 11. The white area 2e is formed on, for example, the inner surface of the dome-shaped portion 2c in the direction of the optical axis O of the objective optical system of the image pickup apparatus 14 when the bending portion 11b is in the neutral state in bending.

FIG. 3 is a cross-sectional view showing a configuration example of the dome-shaped portion 2c of the packaging material 2 provided corresponding to a front-viewing endoscope in the first embodiment.

FIG. 3 shows an example in which the endoscope 1 is a front-viewing endoscope, and the direction of the optical axis O of the objective optical system of the image pickup apparatus 14 is parallel to the longitudinal axis direction of the insertion portion 11. The white area 2e is formed on, for example, the inner surface of the dome-shaped portion 2c in the direction of the optical axis O of the objective optical system of the image pickup apparatus 14 when the bending portion 11b is in the neutral state in bending. Note that the white area 2e may be provided on the outer surface of the transparent or translucent portion of the dome-shaped portion 2c. In the case, adjustment of white balance, which is to be described below, is also performed in the same manner as in the case in which the white area 2e is formed on the inner surface of the dome-shaped portion 2c.

Figure 4:
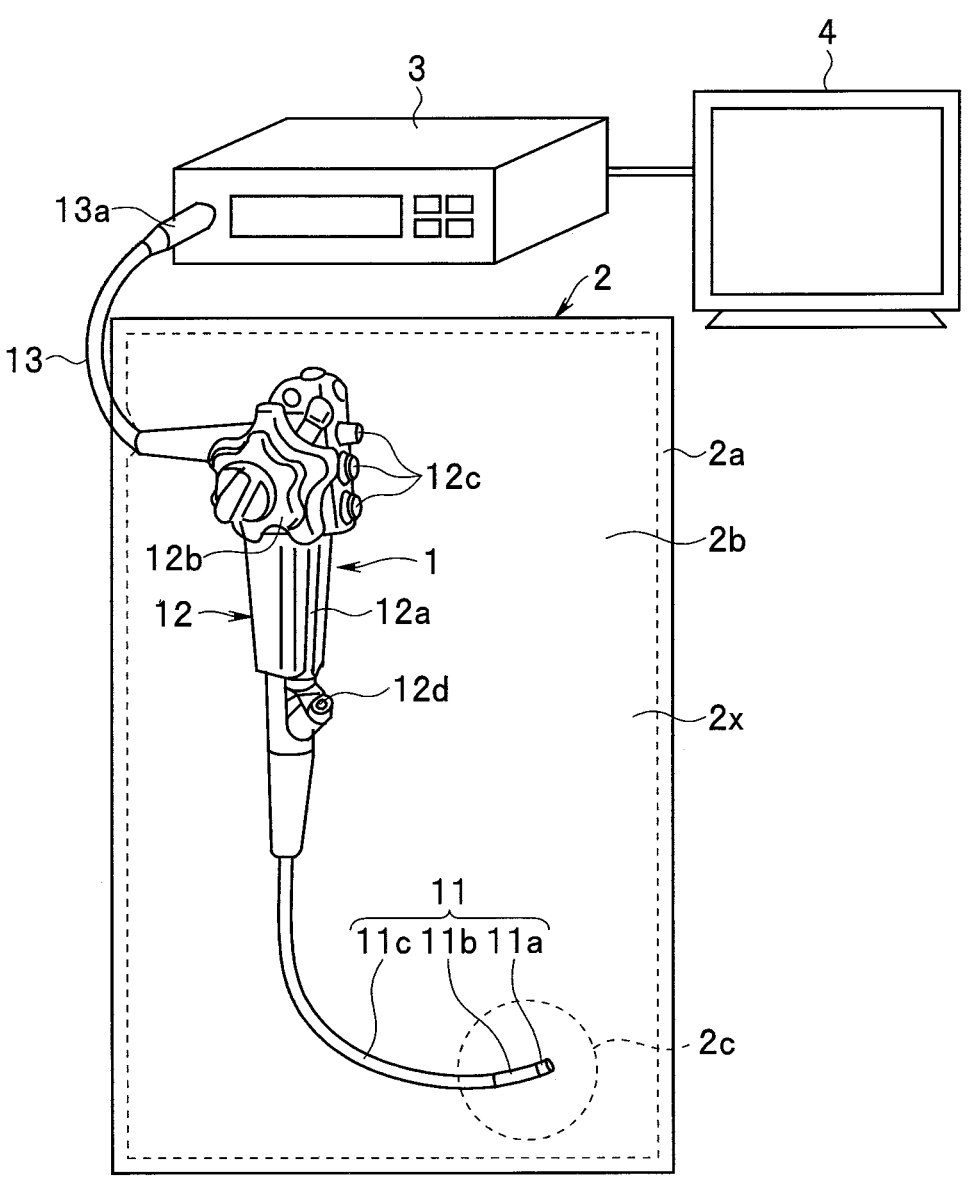
FIG. 4 is a diagram for describing how the endoscope system of the first embodiment is connected to an endoscope processor and pre-use inspection is performed.

FIG. 4 is a diagram for describing how the endoscope system of the first embodiment is connected to an endoscope processor 3 and pre-use inspection is performed.

The endoscope processor 3 is an external apparatus of the endoscope system shown in FIG. 1. To the endoscope processor 3, a monitor 4 is connected, for example. Note that, in the following description, the endoscope processor 3 also serves as a light source device, but the light source device may be configured separately from the endoscope processor 3.

The endoscope processor 3 receives image pickup signals obtained by the image pickup apparatus 14. The endoscope processor 3 performs various image processing such as demosaicking, noise correction, color correction, contrast correction, and gamma correction on the image pickup signals to generate a displayable image signals. The endoscope processor 3 may superimpose various information such as character information and guide information on the image signals.

Note that the endoscope processor 3 may be configured to: includes a processor, such as an ASIC (application specific integrated circuit) including CPU (central processing unit), or the like, or an FPGA (field programmable gate array), which reads and executes a processing program stored in a storage device (or recording medium) such as a memory; and thereby function as each unit. Alternatively, at least part of the endoscope processor 3 may be configured with a dedicated electronic circuit.

In the endoscope 1, the connector 13a arranged outside the packaging material 2 is connected to the endoscope processor 3 in a state in which the insertion portion 11 and the operation portion 12 are packaged in the packaging material 2.

When the connector 13a is connected to the endoscope processor 3, the light guide and signal line are connected to the endoscope processor 3.

The endoscope 1 packaged with the packaging material 2 is then subjected to pre-use inspection before insertion of the endoscope 1 into the subject. For example, the white balance is adjusted and the bending operation is confirmed.

When the endoscope processor 3 and the endoscope 1 are set to white balance mode, the white balance adjustment starts. As described above, since the white area 2e is within the visual field of the image pickup apparatus 14, the white balance adjustment can start without adjustment of the state in bending of the bending portion 11b.

The endoscope processor 3, which also serves as a light source device, supplies illumination light (white light) to the light guide of the endoscope 1. The light guide emits the transmitted illumination light from the illumination window at the distal end. The illumination light emitted from the illumination window when the bending portion 11b is in the neutral state in bending reaches the white area 2e, is reflected by the white area 2e, and becomes return light.

The endoscope processor 3 transmits drive signals and power to the image pickup apparatus 14. The image pickup apparatus 14 picks up optical images of the white area 2e in response to the drive signals, and generates image pickup signals. The image pickup by the image pickup apparatus 14 is sequentially performed, for example, in units of frames, and the image pickup signals related to a moving image of a plurality of frames are generated. The image pickup signals are transmitted to the endoscope processor 3 through the signal line.

The endoscope processor 3 receives the image pickup signals and performs image processing as described above. The endoscope processor 3 performs at least one of, for example, adjusting RGB light amount balance of white light and adjusting the gain of RGB components of the image signals, so that the white balance of the image is appropriate.

At this time, the image signals that have been generated by the endoscope processor 3 may be displayed on the monitor 4 together with, for example, an index indicating the balance of the R signal, G signal, and B signal in the image signals. A user can see the state of white balance adjustment.

Also, the bending operation of the endoscope 1 can be confirmed as follows.

The endoscope 1 may be, for example, an electric bending endoscope that pulls a bending wire by a drive source such as an actuator. In the case, the endoscope processor 3 may transmit the bending control signals to the endoscope 1 to confirm the bending operation of the endoscope 1.

Also, if the endoscope 1 is an endoscope that bends manually, or even if the endoscope 1 is an electric bending endoscope, there are cases in which it is desired to confirm the bending operation by operating the bending operation knob 12b. In the cases, a user operates the bending operation knob 12b of the endoscope 1 packaged in the packaging material 2 by holding the bending operation knob 12b from the outside of the packaging material 2. In the case, the packaging material 2 is made of a flexible material that allows the user to operate the bending operation knob 12b. Also, the portion of the packaging material 2 that accommodates the bending operation knob 12b is formed transparent or translucent so that the bending operation knob 12b is visible from the outside.

As described above, the dome-shaped portion 2c is also provided with a transparent or translucent portion that allows the bending portion 11b to be visible from the outside. Therefore, the user can visually confirm the distal end portion 11a and the bending portion 11b from the outside of the dome-shaped portion 2c as to whether the bending portion 11b has been bent in response to the bending control signals or in response to the operation of the bending operation knob 12b.

In addition, if the bending portion 11b is bent from the neutral state in bending, the view of the outside of the packaging material 2, or the like enters the visual field of the image pickup apparatus 14 through the portion of the dome-shaped portion 2c. Therefore, the user can also confirm the image pickup performance of the image pickup apparatus 14 by observing the monitor 4.

Thus, the bending operation can be confirmed in pre-use inspection inside the dome-shaped portion 2c inside which the sterile condition is kept.

Note that, in place of or in addition to the white area 2e described above, a mark (lattice pattern, or the like) for confirming image pickup performance may be provided within the visual field of the image pickup apparatus 14. As a result, pre-use inspection of the endoscope 1 packaged in the packaging material 2 can further confirm the image pickup performance.

When the pre-use inspection is completed and the endoscope 1 is ready for a step of being inserted into the subject, the packaging material 2 is unsealed. The endoscope 1 is then taken out of the packaging material 2 and an endoscopy is performed.

According to the first embodiment, since the insertion portion 11 and the operation portion 12 of the endoscope 1 are packaged in the packaging material 2, the sterile condition is maintained in the insertion portion 11 and the operation portion 12 while the packaging material 2 is kept sealed.

The connector 13a is arranged outside the packaging material 2. Therefore, the endoscope 1 can be connected to the endoscope processor 3 or the like and can be subjected to pre-use inspection while the packaging material 2 is kept sealed. As a result, the insertion portion 11 and the operation portion 12 do not come into contact with the air in the endoscopy room during pre-use inspection. Furthermore, a time period from unsealing the packaging material 2 to inserting the insertion portion 11 into the subject can be shortened.

The packaging material 2 does not have to be unsealed until just before insertion of the insertion portion 11 into the subject. The packaging material 2 kept sealed can reduce risk (probability) of environmental bacteria adhering to the insertion portion 11 and the operation portion 12 as much as possible, and maintain the sterile condition as much as possible.

Second Embodiment

Figure 5:
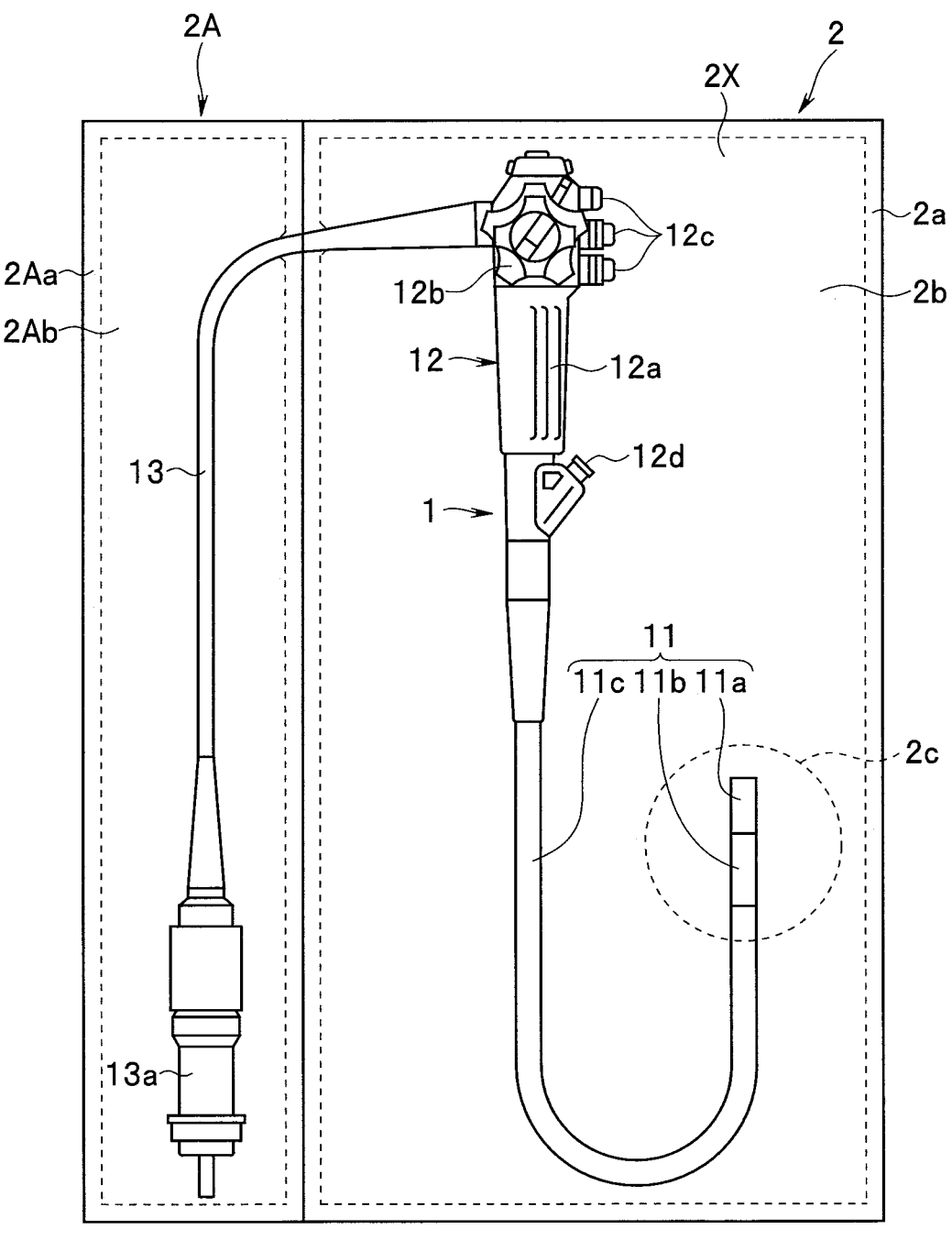
FIG. 5 is a plan view showing a configuration of an endoscope system according to a second embodiment.

FIG. 5 shows a second embodiment of the present disclosure, and is a plan view showing a configuration of an endoscope system. In the second embodiment, components that are the same as the components in the first embodiment are denoted by the same reference numerals and characters, and descriptions are omitted as appropriate, and different points are mainly described.

The endoscope system of the present embodiment further includes a second packaging material 2A in addition to the endoscope 1 and the packaging material 2. While the packaging material 2A is the second packaging material, the packaging material 2 is a first packaging material.

The packaging material 2 packages the insertion portion 11 and the operation portion 12 with the packaging material body 2X to maintain the sterile condition of the insertion portion 11 and the operation portion 12, as is the same as in the first embodiment.

The second packaging material 2A is configured as a sterile packaging material (sterile package). The second packaging material 2A does not package the packaging material 2, but packages a portion of the universal cord 13 arranged outside the packaging material 2 together with the connector 13a. Thus, the sterile condition of the portion of universal cord 13 and the connector 13a is maintained.

The second packaging material 2A has an outer edge portion provided with a seal 2Aa to seal a space 2Ab containing the portion of the universal cord 13 and the connector 13a. Like the seal 2a, the seal 2Aa is also formed, for example, as a heat seal. Note that the portion where the universal cord 13 and the seal 2a or the seal 2Aa overlap may be coated with an adhesive or a filler in addition to a heat seal. Such an adhesive or a filler can improve sealing performance.

Note that the seal 2a and the seal 2Aa are configured to be separated in the portion where the packaging material 2 and the second packaging material 2A are adjacent. This arrangement allows the operation of unsealing the second packaging material 2A to be performed without consequentially unsealing the packaging material 2 as well.

The packaging material 2 and the second packaging material 2A package the entire endoscope 1 without gaps, and maintain the sterile condition of the entire endoscope 1. In other words, the packaging material 2 and the second packaging material 2A together contain the entire endoscope.

When pre-use inspection is performed, the second packaging material 2A is unsealed and the connector 13a is connected to the endoscope processor 3. Here, the packaging material 2 is kept sealed. Therefore, the connector 13a and a portion of the universal cord 13 are maintained in the sterile condition until pre-use inspection is performed.

Then, when the pre-use inspection is completed and the endoscope 1 is ready for a step of being inserted into the subject, the packaging material 2 is unsealed and the endoscope 1 is taken out. An endoscopy is then performed in the same manner as in the first embodiment.

According to the second embodiment described above, substantially the same effects as the effects of the above-described first embodiment are achieved. Also, the connector 13a and a portion of the universal cord 13 are packaged in the second packaging material 2A. Therefore, the sterile condition of the connector 13a and the portion of the universal cord 13 is maintained while the second packaging material 2A is kept sealed.

If only the second packaging material 2A is unsealed, the insertion portion 11 and the operation portion 12 are maintained in the sterile condition by the packaging material 2. In the sterile condition, the connector 13a is connected to the endoscope processor 3 or the like and thereby pre-use inspection of the endoscope 1 can be performed.

Third Embodiment

Figure 6:
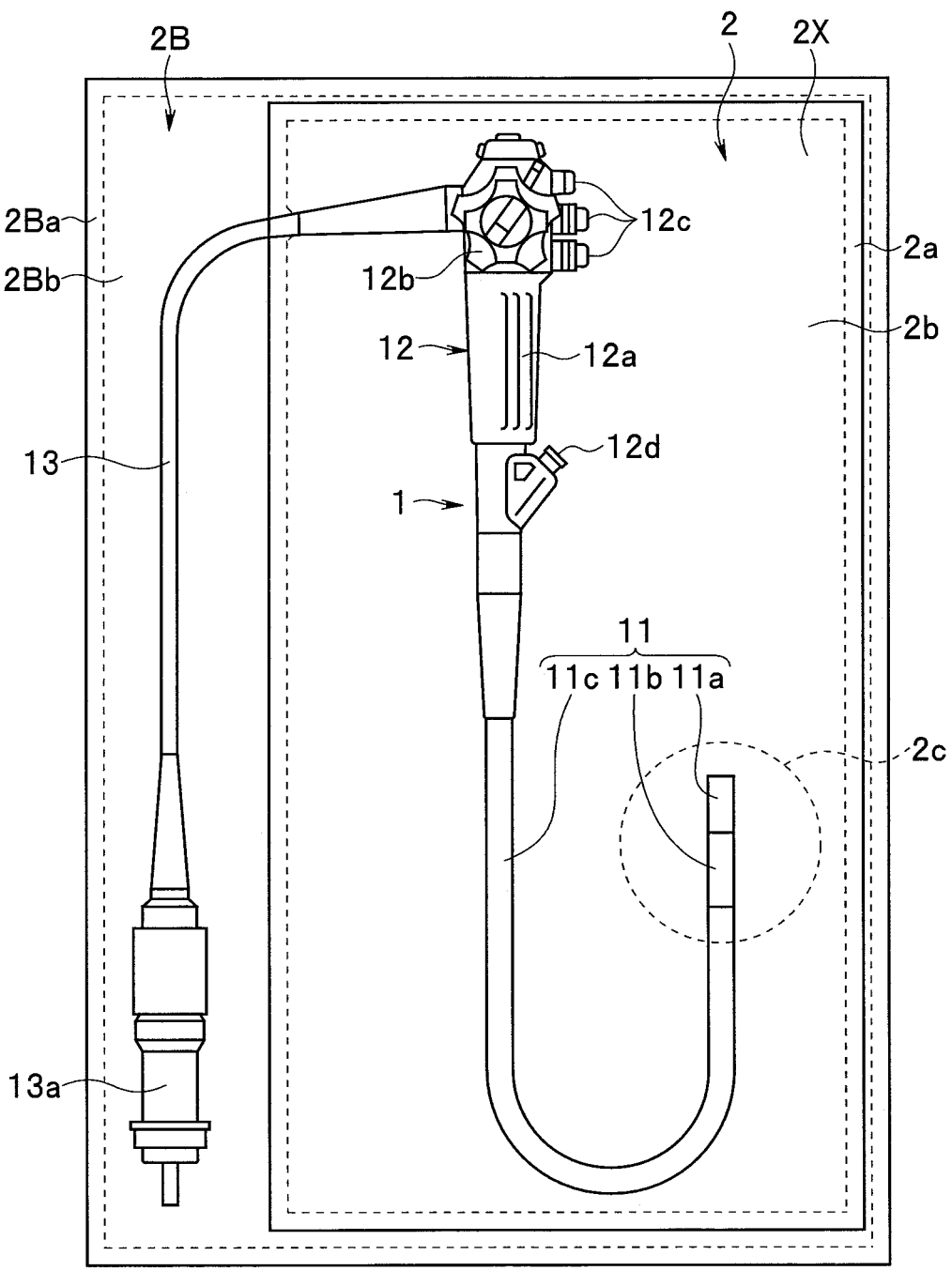
FIG. 6 is a plan view showing a configuration of an endoscope system according to a third embodiment.

FIG. 6 shows a third embodiment of the present disclosure, and is a plan view showing a configuration of an endoscope system. In the third embodiment, components that are the same as the components in the first and the second embodiments are denoted by the same reference numerals and characters, and descriptions are omitted as appropriate, and different points are mainly described.

The endoscope system of the present embodiment further includes a second packaging material 2B in addition to the endoscope 1 and the packaging material 2. While the packaging material 2B is the second packaging material, the packaging material 2 is a first packaging material.

As is the same as in the first and the second embodiments, the packaging material 2 packages the insertion portion 11 and the operation portion 12 with the packaging material body 2X to maintain the sterile condition of the insertion portion 11 and the operation portion 12.

The second packaging material 2B is configured as a sterile packaging material (sterile package), and packages the entire endoscope 1 together with the packaging material 2.

On the outer edge portion of the second packaging material 2B, a seal 2Ba is provided. The second packaging material 2B seals a space 2Bb that contains the connector 13a, a portion of the universal cord 13, and the packaging material 2. The seal 2Ba, like the seal 2a, is also formed, for example, as a heat seal. Note that the portion where the universal cord 13 and the seal 2a overlap may be coated with an adhesive or a filler in addition to a heat seal. Such an adhesive or a filler can improve sealing performance.

The second packaging material 2B packages the connector 13a and a portion of the universal cord 13 arranged outside the packaging material 2 together with the packaging material 2 to maintain the sterile condition. Therefore, the second packaging material 2B maintains the sterile condition of the entire endoscope 1.

The second packaging material 2B is unsealed at a step of pre-use inspection. Therefore, the connector 13a and a portion of the universal cord 13 are maintained in the sterile condition until the pre-use inspection is performed. When the second packaging material 2B is unsealed, the connector 13a can be connected to the endoscope processor 3.

The pre-use inspection is performed with the insertion portion 11 and the operation portion 12 packaged in the packaging material 2. Therefore, the sterile condition of the insertion portion 11 and the operation portion 12 is maintained.

Then, the pre-use inspection is completed, and just before the endoscope 1 is inserted into the subject, the packaging material 2 is unsealed and the endoscope 1 is taken out. Endoscopy is then performed as is the same as in the first and the second embodiments.

According to the third embodiment described above, substantially the same effects as the effects of the above-described the first and the second embodiments are achieved. Together with the packaging material 2, the connector 13a and a portion of the universal cord 13 are packaged in a second packaging material 2B. Therefore, while the second packaging material 2B is kept sealed, the connector 13a and the portion of the universal cord 13 are maintained in the sterile condition.

Even if the second packaging material 2B is unsealed, the sterile condition of the insertion portion 11 and the operation portion 12 is maintained by the packaging material 2. Therefore, the connector 13a can be connected to an external device such as the endoscope processor 3 for pre-use inspection of the endoscope 1.

Fourth Embodiment

Figure 7:
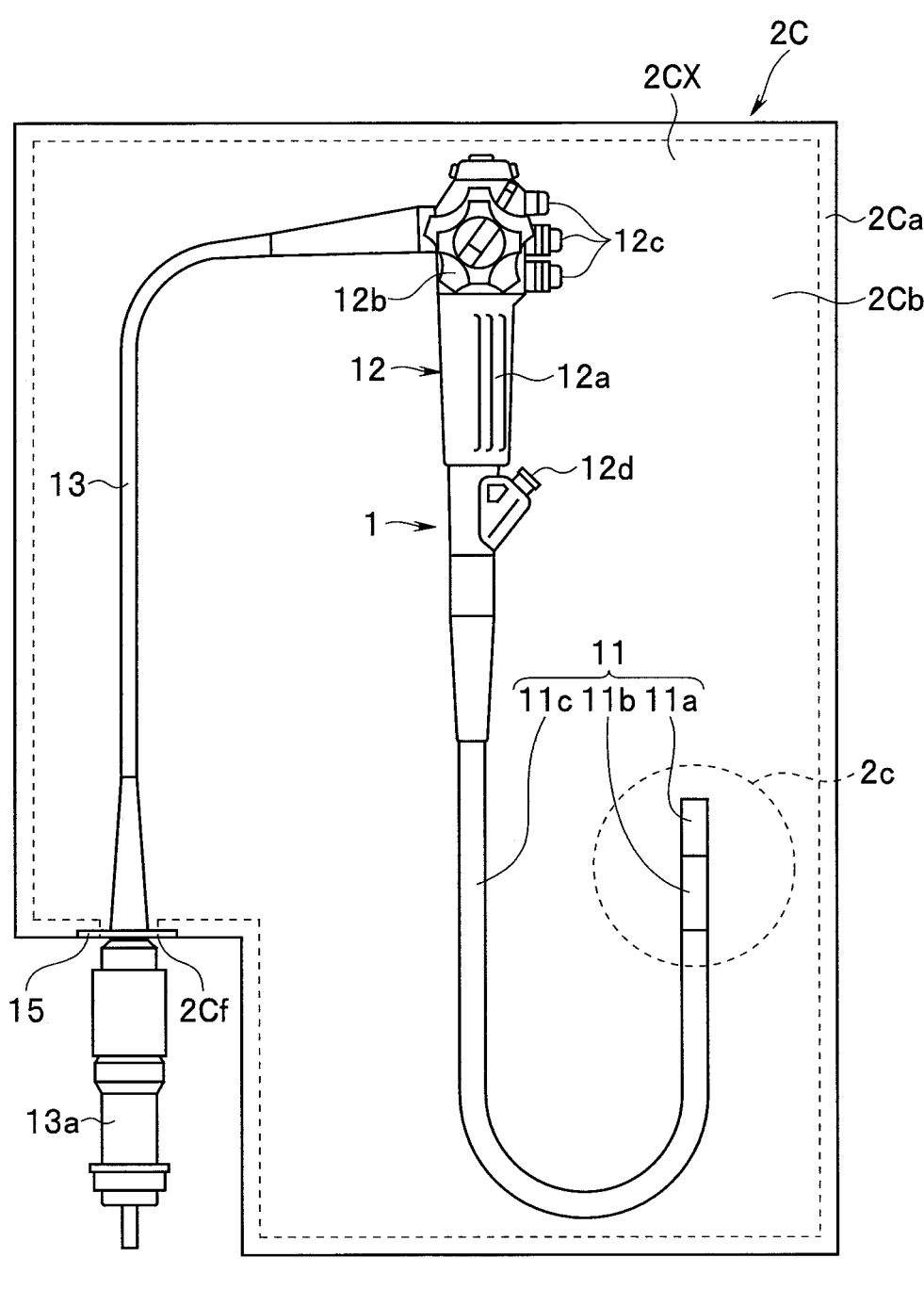
FIG. 7 is a plan view showing a basic configuration of an endoscope system according to a fourth embodiment.
Figure 8:
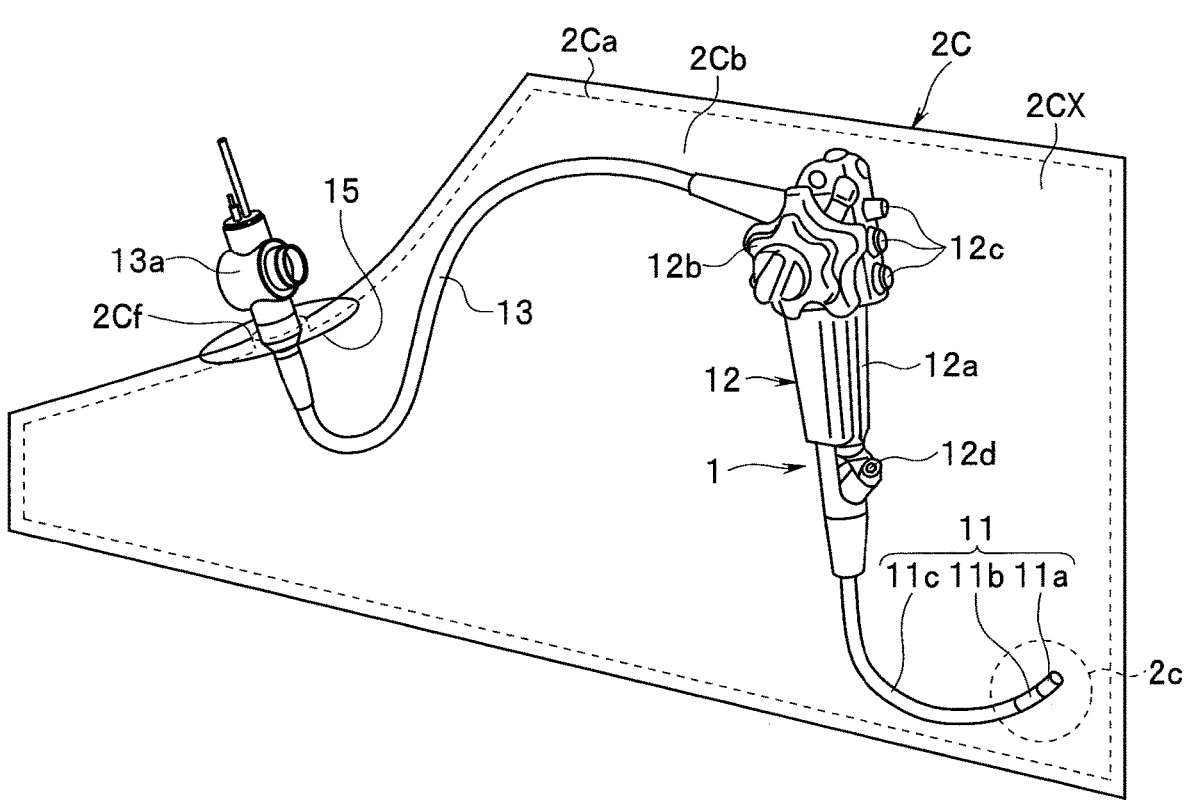
FIG. 8 is a perspective view showing a specific configuration example of the endoscope system in the fourth embodiment.
Figure 9:
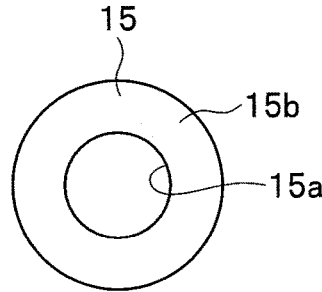
FIG. 9 is a plan view showing a configuration example of a joining member that is joined to a packaging material in the endoscope system of the fourth embodiment.

FIGS. 7 to 9 show a fourth embodiment, and FIG. 7 is a plan view showing a basic configuration of an endoscope system in the fourth embodiment. In the fourth embodiment, components that are the same as the components in the first to the third embodiments are denoted by the same reference numerals and characters, and descriptions are omitted as appropriate, and different points are mainly described.

As shown in FIG. 7, the endoscope system includes the endoscope 1 and a packaging material 2C. The packaging material 2C differs in shape and configuration from the packaging material 2 of the first embodiment.

The packaging material 2C is configured as a sterile packaging material (sterile package). The packaging material 2C packages a first portion of the endoscope 1 with a packaging material body 2CX. Here, the first portion is a portion including the insertion portion 11, the operation portion 12, and a portion of the universal cord 13 excluding the connector 13a. Thus, the sterile condition of the first portion is maintained.

On the outer edge portion of the packaging material 2C, a seal 2Ca is provided. The packaging material 2C forms a space 2Cb that contains the insertion portion 11, the operation portion 12, and the portion of the universal cord 13 excluding the connector 13a. The seal 2Ca, like the seal 2a, is also formed, for example, as a heat seal. The connector 13*a*, which is a second portion of the endoscope 1, is arranged outside the outer edge portion of the packaging material 2C (the outer edge portion of the packaging material body 2CX).

FIG. 8 is a perspective view showing a specific configuration example of the endoscope system according to the fourth embodiment. FIG. 8 shows a more specific example of the endoscope system having the basic configuration shown in FIG. 7.

In the specific example of FIG. 8, the connector 13*a* is arranged upward. The edge of the packaging material 2C adjacent to the connector 13*a* is formed to be a smooth curved line to facilitate connection of the connector 13*a* to the endoscope processor 3.

Figure 10:
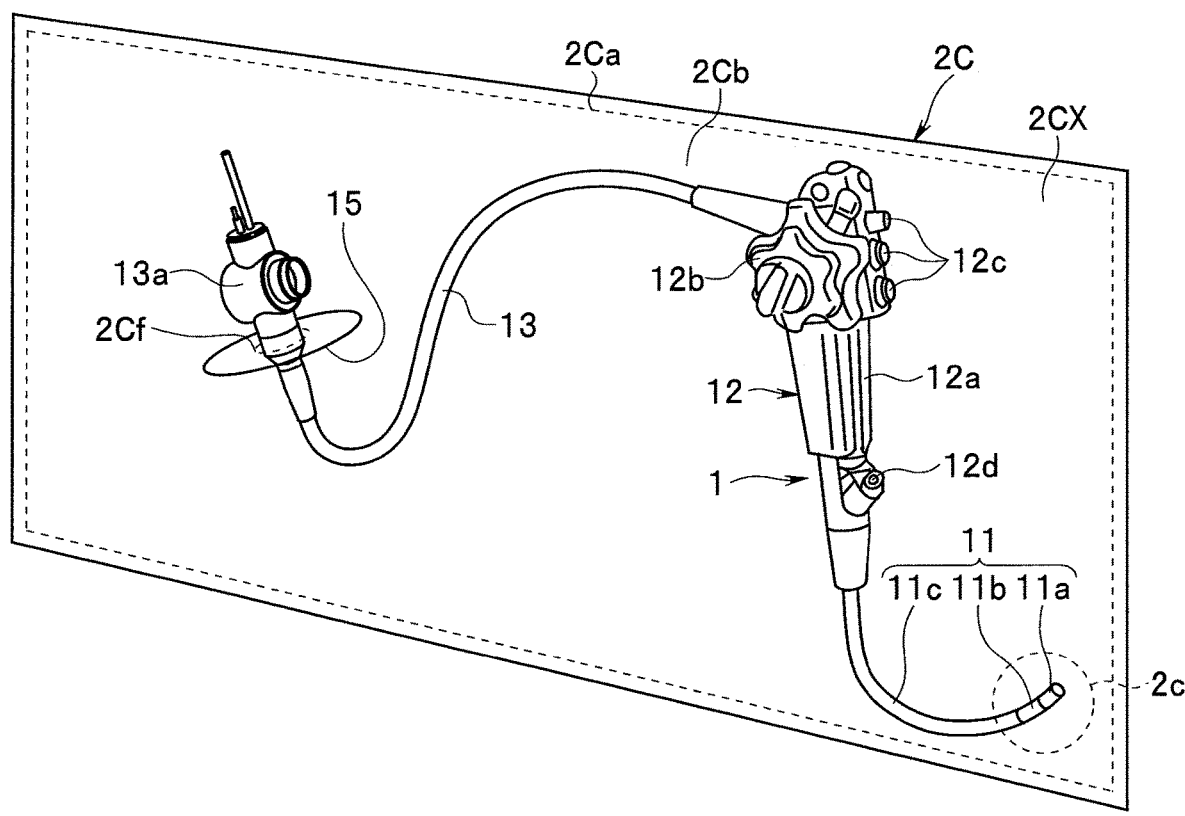
FIG. 10 is a perspective view showing a modification of a joining position of the packaging material and the joining member in the endoscope system of the fourth embodiment.

The packaging material 2C is provided with a hole 2Cf, and the connector 13*a* extends from the hole 2Cf. The hole 2Cf is provided, for example, in a portion of the seal 2Ca at the outer edge portion of the packaging material 2C. Note that the position of the hole 2Cf is not limited to the outer edge portion of the packaging material 2C, and may be a center, a corner, or the like of the packaging material 2C. As is described below, a joining member 15 forming a portion of the seal may be adjusted to be located at a predetermined position that facilitates heat sealing (see FIG. 10). FIG. 10 is a perspective view showing a modification of the joining position of the packaging material 2C and the joining member 15 in the endoscope system of the fourth embodiment. In the example of FIG. 10, the packaging material 2C is rectangular, and the joining member 15 is arranged in a central portion (or near the central portion) of the packaging material body 2CX.

As shown in FIGS. 7 and 8, a joining member 15 joined to the packaging material 2C is provided on the proximal end side of the connector 13*a* or the distal end side of the portion of the universal cord 13 excluding the connector 13*a*.

FIG. 9 is a plan view showing a configuration example of the joining member 15 to be joined to the packaging material 2C in the endoscope system of the fourth embodiment.

The joining member 15 is, for example, a resin member formed in a flat ring shape made of the same resin material as the packaging material 2C. The joining member 15 has a ring-shaped inner circumference 15*a* airtightly joined to the proximal end side of the connector 13*a* or the distal end side of the portion of the universal cord 13 excluding the connector 13*a*. Here, the inner circumference 15*a* of the joining member 15 may be airtightly joined to the proximal end side of the connector 13*a* or the distal end side of the portion of the universal cord 13 excluding the connector 13*a*, for example, by an adhesive.

In addition, the joining member 15 is airtightly joined to the packaging material 2C around the hole 2Cf, on an outer circumference side 15*b*. Therefore, the diameter of the hole 2Cf is larger than the inner diameter of the ring-shaped joining member 15 and smaller than the outer diameter of the joining member 15. Here, the airtight joining between the outer circumference side 15*b* of the joining member 15 and the packaging material 2C may be heat sealing by heat welding, for example.

The packaging material 2C and the joining member 15, which have been joined together, seal the space 2Cb that contains the first portion, which includes the insertion portion 11, the operation portion 12, and the portion of the universal cord 13 excluding the connector 13*a*. Thus, the proximal end side of the connector 13*a* or the distal end side of the portion of the universal cord 13 excluding the connector 13*a* is fixed to the packaging material 2C by the joining member 15. The connector 13*a*, which is the second portion of the endoscope 1, is arranged outside the outer edge portion of the packaging material 2C.

Pre-use inspection is performed while the endoscope 1 excluding the connector 13*a* is sealed with the packaging material 2C and the joining member 15, basically in the same manner as in the first to the third embodiments. The sealing prevents the first portion of the endoscope 1 from coming into contact with air in the endoscopy room during the pre-use inspection. Furthermore, a time period from unsealing the packaging material 2C to inserting the insertion portion 11 into the subject can be shortened.

Then, the pre-use inspection is completed, and just before insertion of the endoscope 1 into the subject, the packaging material 2C is unsealed. The endoscope 1 is then taken out of the packaging material 2C and endoscopy is performed, as is basically the same as in the first to the third embodiments.

Here, since the joining member 15 is provided at or near the connector 13*a*, the operation of the endoscope 1 is not hindered if the joining member 15 remains joined to the endoscope 1. For example, the joining member 15 may be configured so as to be provided with a fragile portion so that the joining member 15 is separated from the endoscope 1 by an external force for unsealing the packaging material 2C. The configuration is because the joining member 15 does not remain joined to the endoscope 1 after unsealing.

If the joining member 15 is configured to be separated from the endoscope 1, the joining member 15 may be provided at a desired position of the connector 13*a* or a desired position of the portion of the universal cord 13 excluding the connector 13*a*.

According to the fourth embodiment described above, substantially the same effects as the effects of the above-described first to third embodiments can be achieved. Furthermore, the endoscope 1 is packaged in the packaging material 2C with the joining member 15. Therefore, it is not necessary to directly join the packaging material 2 to the endoscope 1 as in the first embodiment, facilitating the joining operation of the packaging material 2C.

Note that the present disclosure is not limited to the embodiment exactly the same as the above description, and can be embodied by modifying the components without departing from the gist of the present disclosure at the implementation stage. Moreover, various aspects of the disclosure can be formed by appropriate combinations of the plurality of components disclosed in the above embodiments. For example, some components may be omitted from all components shown in the embodiments. Furthermore, components across different embodiments may be combined as appropriate. As described above, it goes without saying that various modifications and applications are possible without departing from the gist of the disclosure.

1. An endoscope system comprising:
   an endoscope including an insertion portion, an operation portion, and a connector configured to be connected to an external apparatus, the insertion portion including a bendable bending portion, the operation portion being connected to the insertion portion;
   a packaging material configured to package the insertion portion and the operation portion to maintain a sterile condition of the insertion portion and the operation portion, and to have the connector arranged outside; and a dome-shaped portion, formed in the packaging material, including a space inside which the bending portion can freely bend and inside which the bending portion is arranged.

2. The endoscope system according to example 1, wherein the dome-shaped portion is configured so that the bending portion is visible from outside.

3. The endoscope system according to example 1, wherein the dome-shaped portion includes, at least in part, a white area for white balance.

4. The endoscope system according to example 3, wherein an image pickup apparatus is disposed at a distal end portion of the insertion portion, and the white area is disposed in an optical axis direction of the image pickup apparatus in a state in which the bending portion is not bent.

5. The endoscope system according to example 1, further comprising a second packaging material configured to package the connector arranged outside the packaging material and to maintain a sterile condition of the connector.

6. The endoscope system according to example 5, wherein the second packaging material does not package the packaging material, and the packaging material and the second packaging material package the endoscope as a whole without gaps and maintain a sterile condition of the endoscope as a whole.

7. The endoscope system according to example 5, wherein the second packaging material packages the packaging material and the connector to maintain a sterile condition of the packaging material and the connector.

8. The endoscope system according to example 1, wherein one end of a universal cord is connected to the operation portion, and the connector is provided at another end of the universal cord.

9. The endoscope system according to example 8, wherein the connector or a portion of the universal cord excluding the connector is provided with a joining member that is joined to the packaging material.

10. The endoscope system according to example 9, wherein the joining member is a resin member that is joined to the packaging material by heat welding.

11. The endoscope system according to example 1, wherein the endoscope is a single-use endoscope that is disposed of after a single use.

12. A packaging material for endoscope, the material comprising:

a packaging material body configured to package a first portion of an endoscope;

a dome-shaped portion, included in the packaging material body, having a space inside; and a seal formed at a predetermined position of the packaging material body, the seal having a second portion of the endoscope arranged outside the predetermined position.

13. The packaging material for endoscope according to example 12, wherein the predetermined position is an outer edge portion of the packaging material body.

14. The packaging material for endoscope according to example 13, wherein the first portion of the endoscope includes an insertion portion and an operation portion, the insertion portion including a bendable bending portion, the operation portion being connected to the insertion portion, and the second portion of the endoscope includes a connector configured to be connected to an external apparatus.

15. The packaging material for endoscope according to example 14, wherein the bending portion is arranged in the space of the dome-shaped portion.

16. The packaging material for endoscope according to example 15, wherein the endoscope is provided with a universal cord between the operation portion and the connector, and the packaging material for endoscope is sealed in a state in which the universal cord is passed through the seal.

17. The packaging material for endoscope according to example 12, wherein the predetermined position is a central portion of the packaging material body.

What is claimed is:

1. An endoscope system, comprising:

an endoscope including an insertion portion, an operation portion, and a connector configured to be connected to an external apparatus, wherein the insertion portion includes a bending portion and wherein the operation portion is connected to the insertion portion;

a packaging material, wherein the packaging material contains at least the insertion portion or the operation portion in a sterile environment; and a dome-shaped portion formed in the packaging material, wherein the dome-shaped portion is a self-standing dome shape that differs from a shape of the packaging material, wherein the dome-shaped portion defines a space, wherein at least a distal section of the bending portion is located inside the space, wherein, in a maximum bent position, the distal section of the bending portion does not contact an inner surface of the dome shaped portion, and wherein the connector is disposed outside of the packaging material.

2. The endoscope system according to claim 1, wherein the bending portion is visible through the packaging material of the dome-shaped portion.

3. The endoscope system according to claim 2, wherein the dome-shaped portion includes a transparent or translucent region on at least one side of the packaging material.

4. The endoscope system according to claim 1, wherein at least a part of the dome-shaped portion includes a white area.

5. The endoscope system according to claim 4, wherein the endoscope further includes an image pickup apparatus at a distal end of the insertion portion, and wherein, when the bending portion is not bent, an optical axis of the image pickup apparatus intersects the white area.

6. The endoscope system according to claim 1, wherein the packaging material is a first package material and the sterile environment is a first sterile environment, wherein the endoscope system further comprises a second packaging material, and wherein the second packaging material contains the connector in a second sterile environment.

7. The endoscope system according to claim 6, wherein there is at least some overlap between the two packaging materials to maintain the sterile environment, and wherein the first packaging material and the second packaging material together contain the entire endoscope.

8. The endoscope system according to claim 1, wherein the packaging material is a first package material and the sterile environment is a first sterile environment, wherein the endoscope system further comprises a second packaging material, and wherein the second packaging material contains the connector and the first packaging material containing the insertion portion and the operation portion in a second sterile environment.

9. The endoscope system according to claim 1, wherein the endoscope further includes a universal cord, wherein a first end of the universal cord is connected to the operation portion, and wherein a second end of the universal cord includes the connector.

10. The endoscope system according to claim 9, further comprising a sealing material, wherein the sealing material joins a part of the universal cord and the packaging material.

11. The endoscope system according to claim 10, wherein the sealing material has a composition including a resin, and wherein the sealing material is joined to the packaging material by a heat weld.

12. The endoscope system according to claim 1, wherein the endoscope is a single-use endoscope.

13. An endoscope system, comprising:

an endoscope including an insertion portion, an operation portion, and a connector configured to be connected to an external apparatus, wherein the insertion portion includes a bending portion and wherein the operation portion is connected to the insertion portion; and a packaging material sealed to form an interior space, where the interior space is a sterile environment, wherein a portion of the packaging material forming the interior space includes a dome-shaped portion having a self-standing dome shape, and wherein the insertion portion is located within the interior space with the bending portion located within the dome-shaped portion.

14. The endoscope system according to claim 13, wherein the dome-shaped portion defines a space, wherein at least a distal section of the bending portion is located inside the space, wherein, in a maximum bent position, the distal section of the bending portion does not contact an inner surface of the dome shaped portion, and wherein the connector is disposed outside of the packaging material.

\* \* \* \* \*